(12) United States Patent
Manzo et al.

(45) Date of Patent: Aug. 7, 2012
(10) Patent No.: US 8,236,297 B2

(54) METHOD OF TREATING LACTOSE INTOLERANCE USING GENETICALLY ENGINEERED BACTERIA

(76) Inventors: Kenneth Manzo, Shohola, PA (US); Jay Sharma, San Pedro, CA (US)

( * ) Notice: Subject to any disclaimer, the term of this patent is extended or adjusted under 35 U.S.C. 154(b) by 653 days.

(21) Appl. No.: 11/871,113

(22) Filed: Oct. 11, 2007

(65) Prior Publication Data

US 2009/0098087 A1  Apr. 16, 2009

(51) Int. Cl.
*A01N 63/00* (2006.01)
*C12N 15/00* (2006.01)
*C12N 1/20* (2006.01)

(52) U.S. Cl. .................. 424/93.45; 424/93.1; 424/93.2; 435/320.1; 435/252.9

(58) Field of Classification Search ........................ None
See application file for complete search history.

(56) References Cited

U.S. PATENT DOCUMENTS

| | | | |
|---|---|---|---|
| 2,762,749 A | 9/1956 | Myers | |
| 3,620,924 A | 11/1971 | Harvey | |
| 4,179,335 A | 12/1979 | Long | |
| 4,237,230 A | 12/1980 | Iida | |
| 4,323,651 A | 4/1982 | Long | |
| 5,633,012 A | 5/1997 | Ford | |
| 5,952,021 A | 9/1999 | Santus | |
| 6,008,027 A | 12/1999 | Langner | |
| 6,110,456 A | 8/2000 | During | |
| 6,562,339 B2 | 5/2003 | Eisenhardt | |
| 6,599,882 B1 | 7/2003 | Rogoff | |
| 6,833,260 B1 | 12/2004 | Ruch | |
| 2004/0121041 A1 | 6/2004 | Van Beckhoven et al. | |
| 2004/0265856 A1* | 12/2004 | Peltonen et al. | 435/6 |
| 2005/0100535 A1 | 5/2005 | Farmer | |
| 2007/0266451 A1* | 11/2007 | Chen et al. | 800/14 |

FOREIGN PATENT DOCUMENTS

| | | |
|---|---|---|
| JP | 51098244 A1 | 6/1978 |
| JP | 2003 285218 A1 | 3/2005 |
| KR | 2001 00027768 A1 | 11/2002 |
| KR | 2002 000004436 A1 | 7/2003 |
| KR | 2002 000072758 A1 | 5/2004 |

OTHER PUBLICATIONS

Naim et al., 1991, J Biol. Chem. 266:12313-12320.*
Rolfe et al., 2000, J. Nutr. 130396S-402S.*
Mantei, N. et al. "Complete primary structure of human and rabbit lactase-phlorizin hydrolase[. . . ]", EMBO J., 1988, v.7, No. 9, p. 2705-2713.
Levri, K. et al. "Do probiotics reduce adult lactose intolerance?", J. Fam. Pract., 2005, v. 54, No. 7 p. 613-620.
Saltzman, J. et al. "A randomized trial of *Lactobacillus acidophilus* BG2FO4 to treat lactose intolerance", Am. J. Clin. Nutr, 1999, v. 69, p. 140-146.

(Continued)

*Primary Examiner* — Robert M Kelly
*Assistant Examiner* — Kelaginamane T Hiriyanna
(74) *Attorney, Agent, or Firm* — Sanjesh Prabha Sharma; Chen Yoshimura LLP (57) ABSTRACT

The present invention relates to genetically engineered bacteria that are able to colonize the mammalian intestine and actively produce mammalian lactase (lactose-phlorizin hydrolase or LPH). This lactose-digesting enzyme is stable and active under the conditions normally found in the mammalian small intestine. Experimental subjects colonized with the genetically engineered bacteria show improved ability to digest lactose in dairy foods.

5 Claims, 1 Drawing Sheet

OTHER PUBLICATIONS

Hertzler, S. et al. "Kefir improves lactose digestion and tolerance in adults with lactose maldigestion", J. Am. Diet. Assoc., 2003, v. 103, No. 5, p. 582-587.

Jost et al. Functional diversity and interactions between the repeat domains of rat intestinal lactase, Biochem. J. 327:95-103 (1997).

USP27, official monograph p. 1062-1063 (2004).

* cited by examiner

SEQUENCE LISTING

```
<160> NUMBER OF SEQ ID NOS: 9

<210> SEQ ID NO 1
<211> LENGTH: 6274
<212> TYPE: DNA
<213> ORGANISM: Homo sapiens

<400> SEQUENCE: 1
gttcctagaa aatggagctg tcttggcatg tagtctttat tgccctgcta agttttcat      60 gctggggtc  agactgggag tctgatagaa atttcatttc caccgctggt cctctaacca    120
atgacttgct gcacaacctg agtggtctcc tgggagacca gagttctaac tttgtagcag    180
gggacaaaga catgtatgtt tgtcaccagc cactgcccac tttcctgcca gaatacttca    240
gcagtctcca tgccagtcag atcacccatt ataaggtatt tctgtcatgg gcacagctcc    300
tcccagcagg aagcacccag aatccagacg agaaaacagt gcagtgctac cggcgactcc    360
tcaaggccct caagactgca cggcttcagc ccatggtcat cctgcaccac cagaccctcc    420
```

```
ctgccagcac cctccggaga accgaagcct ttgctgacct cttcgccgac tatgccacat    480
tcgccttcca ctccttcggg gacctagttg ggatctggtt caccttcagt gacttggagg    540
aagtgatcaa ggagcttccc caccaggaat caagagcgtc acaactccag accctcagtg    600
atgcccacag aaaagcctat gagatttacc acgaaagcta tgcttttcag ggcggaaaac    660
tctctgttgt cctgcgagct gaagatatcc cggagctcct gctagaacca cccatatctg    720
cgcttgccca ggacacggtc gatttcctct ctcttgattt gtcttatgaa tgccaaaatg    780
aggcaagtct gcggcagaag ctgagtaaat tgcagaccat tgagccaaaa gtgaaagttt    840
tcatcttcaa cctaaaactc ccagactgcc cctccaccat gaagaaccca gccagtctgc    900
tcttcagcct ttttgaagcc ataaataaag accaagtgct caccattggg tttgatatta    960
atgagtttct gagttgttca tcaagttcca agaaaagcat gtcttgttct ctgactggca   1020
gcctggccct tcagcctgac cagcagcagg accacgagac cacggactcc tctcctgcct   1080
ctgcctatca gagagtctgg gaagcatttg ccaatcagtc cagagcggaa agggatgcct   1140
tcctgcagga tactttccct gaaggcttcc tctggggtgc ctccacagga gcctttaacg   1200
tggaaggagg ctgggccgag ggtgggagag gggtgagcat ctgggatcca cgcaggcccc   1260
tgaacaccac tgagggccaa gcgacgctgg aggtggccag cgacagttac cacaaggtag   1320
cctctgacgt cgccctgctt tgcggcctcc gggctcaggt gtacaagttc tccatctcct   1380
ggtcccggat cttccccatg gggcacggga gcagcccag cctcccaggc gttgcctact   1440
acaacaagct gattgacagg ctacaggatg cgggcatcga gcccatggcc acgctgttcc   1500
actgggacct gcctcaggcc ctgcaggatc atggtggatg gcagaatgag agcgtggtgg   1560
atgccttcct ggactatgcg gccttctgct tctccacatt tggggaccgt gtgaagctgt   1620
gggtgacctt ccatgagccg tgggtgatga gctacgcagg ctatggcacc ggccagcacc   1680
ctcccggcat ctctgaccca ggagtggcct cttttaaggt ggctcacttg gtcctcaagg   1740
ctcatgccag aacttggcac cactacaaca gccatcatcg cccacagcag caggggcacg   1800
tgggcattgt gctgaactca gactgggcag aaccctgtc tccagagagg cctgaggacc   1860
tgagagcctc tgagcgcttc ttgcacttca tgctgggctg gtttgcacac cccgtctttg   1920
tggatggaga ctacccagcc accctgagga cccagatcca acagatgaac agacagtgct   1980
cccatcctgt ggctcaactc cccgagttca gagaggcaga gaagcagctc ctgaaaggct   2040
ctgctgattt tctgggtctg tcgcattaca cctcccgcct catcagcaac gccccacaaa   2100
acacctgcat ccctagctat gataccattg gaggcttctc ccaacacgtg aaccatgtgt   2160
ggccccagac ctcatcctct tggattcgtg tggtgccctg ggggataagg aggctgttgc   2220
agtttgtatc cctggaatac acaagaggaa agttccaat ataccttgcc gggaatggca   2280
tgcccatagg ggaaagtgaa aatctctttg atgattcctt aagagtagac tacttcaatc   2340
aatatatcaa tgaggtgctc aaggctatca aggaagactc tgtggatgtt cgttcctaca   2400
ttgctcgttc cctcattgat ggcttcgaag gcccttctgg ttacagccag cggtttggcc   2460
tgcaccacgt caacttcagc gacagcagca agtcaaggac tcccaggaaa tctgcctact   2520
ttttcactag catcatagaa aagaacggtt tcctcaccaa gggggcaaaa agactgctac   2580
cacctaatac agtaaacctc ccctccaaag tcagagcctt cactttttcca tctgaggtgc   2640 cctccaaggc taaagtcgtt tgggaaaagt ctccagcca acccaagttc gaaagagatt   2700
tgttctacca cggacgtttt cgggatgact ttctgtgggg cgtgtcctct tccgcttatc   2760
agattgaagg cgcgtgggat gccgatggca aaggccccag catctgggat aactttaccc   2820
```

```
acacaccagg gagcaatgtg aaagacaatg ccactggaga catcgcctgt gacagctatc    2880
accagctgga tgccgatctg aatatgctcc gagctttgaa ggtgaaggcc taccgcttct    2940
ctatctcctg gtctcggatt tcccaactg ggagaaacag ctctatcaac agtcatgggg     3000
ttgattatta caacaggctg atcaatggct tggtggcaag caacatcttt cccatggtga    3060
cattgttcca ttgggacctg ccccaggccc tccaggatat cggaggctgg gagaatcctg    3120
ccttgattga cttgtttgac agctacgcag acttttgttt ccagaccttt ggtgatagag    3180
tcaagttttg gatgactttt aatgagccca tgtacctggc atggctaggt tatggctcag    3240
gggaatttcc cccaggggtg aaggaccag gctgggcacc atataggata gcccacaccg     3300
tcatcaaagc ccatgccaga gtctatcaca cgtacgatga aaatacagg caggagcaga     3360 aggggggtcat ctcgctgagc ctcagtacac actgggcaga gcccaagtca ccaggggtcc   3420
ccagagatgt ggaagccgct gaccgaatgc tgcagttctc cctgggctgg tttgctcacc    3480 ccattttag aaacggagac tatcctgaca ccatgaagtg gaaagtgggg aacaggagtg      3540
aactgcagca cttagccacc tcccgcctgc caagcttcac tgaggaagag aagaggttca    3600
tcagggcgac ggccgacgtc ttctgcctca acacgtacta ctccagaatc gtgcagcaca    3660
aaacacccag gctaaaccca ccctcctacg aagacgacca ggagatggct gaggaggagg    3720
acccttcgtg gccttccacg gcaatgaaca gagctgcgcc ctgggggacg cgaaggctgc    3780
tgaactggat caaggaagag tatggtgaca tccccattta catcaccgaa aacggagtgg    3840
ggctgaccaa tccgaacacg gaggatactg ataggatatt ttaccacaaa acctacatca    3900
atgaggcttt gaaagcctac aggctcgatg gtatagacct tcgagggtat gtcgcctggt    3960
ctctgatgga caactttgag tggctaaatg gctacgggt caagtttgga ctgtaccatg     4020
ttgatttcaa caacacgaac aggcctcgca cagcaagagc ctccgccagg tactacacag    4080
aggtcattac caacaacggc atgccactgg ccagggagga tgagtttctg tacgacggt     4140 ttcctgaggg cttcatctgg agtgcagctt ctgctgcata tcagattgaa ggtgcgtgga    4200
gagcagatgg caaaggactc agcatttggg acacgttttc tcacacacca ctgagggttg    4260
agaacgatgc cattggagac gtggcctgtg acagttatca caagattgct gaggatctgg    4320
tcaccctgca gaacctgggt gtgtcccact accgttttc catctcctgg tctcgcatcc     4380
tccctgatgg aaccaccagg tacatcaatg aagcgggcct gaactactac gtgaggctca    4440
tcgatacact gctggccgcc agcatccagc cccaggtgac catttaccac tgggacctac    4500
cacagacgct ccaagatgta ggaggctggg agaatgagac catcgtgcag cggtttaagg    4560
agtatgcaga tgtgctcttc cagaggctgg gagacaaggt gaagttttgg atcacgttga    4620
atgagccctt tgtcattgct taccaggct atggctacgg aacagcagct ccaggagtct    4680
ccaataggcc tggcactgcc ccctacattg ttggccacaa tctaataaag gctcatgctg    4740
aggcctggca tctgtacaac gatgtgtacc gcgccagtca aggtggcgtg atttccatca    4800
ccatcagcag tgactgggct gaacccagag atccctctaa ccaggaggat gtggaggcag    4860
ccaggagata tgttcagttc atgggaggct ggtttgcaca tcctattttc aagaatggag    4920
attacaatga ggtgatgaag acgcggatcc gtgacaggag cttggctgca ggcctcaaca    4980
agtctcggct gccagaattt acagagagtg agaagaggag gatcaacggc acctatgact    5040
tttttgggtt caatcactac accactgtcc tcgcctacaa cctcaactat gccactgcca    5100
tctcttcttt tgatgcagac agaggagttg cttccatcgc agatcgctcg tggccagact    5160
ctggctcctt ctggctgaag atgacgcctt ttggcttcag gaggatcctg aactggttaa    5220
```

```
aggaggaata caatgaccct ccaatttatg tcacagagaa tggagtgtcc cagcgggaag      5280
aaacagacct caatgacact gcaaggatct actaccttcg gacttacatc aatgaggccc      5340
tcaaagctgt gcaggacaag gtggaccttc gaggatacac agtttggagt gcgatggaca      5400
attttgagtg ggccacaggc ttttcagaga gatttggtct gcattttgtg aactacagtg      5460
acccttctct gccaaggatc cccaaagcat cagcgaagtt ctacgcctct gtggtccgat      5520
gcaatggctt ccctgacccc gctacagggc ctcacgcttg tctccaccag ccagatgctg      5580
gacccaccat cagccccgtg agacaggagg aggtgcagtt cctggggcta atgctcggca      5640
ccacagaagc acagacagct ttgtacgttc tcttttctct tgtgcttctt ggagtctgtg      5700
gcttggcatt tctgtcatac aagtactgca agcgctctaa gcaagggaaa acacaacgaa      5760
gccaacagga attgagcccg gtgtcttcat tctgatgagt taccacctca agttctatga      5820
agcaggccta gtttcttcat ctatctttac cggccaccaa acaccttagg gtcttagact      5880
ctgctgatac tggacttctc cataaagtcc tgctgcaccg ttagagatga ctttaatctt      5940
gaatgatttc gacttgctga gtaaaatgga aatatctcca tcttgctcca gtatcagagt      6000
tcatttgggc atttgagaag caagtagctc ttgcggaaac gtgtagatac tggtctagtg      6060
ggtctgtgaa ccacttaatt gaacttaaca gggctgtttt aagtttcaga gttgttaagg      6120
gttgttaagg gagcaaaaac cgtaaaaatc cttcctataa gaagaaatca actccattgc      6180
atagactgca atatcatctc ctgcccttct gcaagctctc cctagcttca catcttgtgt      6240
tttccagaaa ataaaaacag aagactgtcc tttc                                  6274

<210> SEQ ID NO 2
<211> LENGTH: 42
<212> TYPE: DNA
<213> ORGANISM: artificial sequence
<220> FEATURE:
<223> OTHER INFORMATION: Primer LPH1

<400> SEQUENCE: 2
aaagaattcg ttcctagaaa atggagctgt cttggcatgt ag                         42

<210> SEQ ID NO 3
<211> LENGTH: 40
<212> TYPE: DNA
<213> ORGANISM: artificial sequence
<220> FEATURE:
<223> OTHER INFORMATION: Primer CLPH1300

<400> SEQUENCE: 3
ttgcatgcat aagcttaaat ttctgtcgga ttccccagtc                            40

<210> SEQ ID NO 4
<211> LENGTH: 25
<212> TYPE: DNA
<213> ORGANISM: artificial sequence
<220> FEATURE:
<223> OTHER INFORMATION: Primer LPH2841

<400> SEQUENCE: 4
aaagacaatg ccactggaga catcg                                            25

<210> SEQ ID NO 5
<211> LENGTH: 25
<212> TYPE: DNA
<213> ORGANISM: artificial sequence
<220> FEATURE:
<223> OTHER INFORMATION: Primer CLPH3600
```

-continued

```
<400> SEQUENCE: 5
tgaacctctt ctcttcctca gtgaa                                            25

<210> SEQ ID NO 6
<211> LENGTH: 25
<212> TYPE: DNA
<213> ORGANISM: artificial sequence
<220> FEATURE:
<223> OTHER INFORMATION: Primer LPH3541

<400> SEQUENCE: 6
aactgcagca cttagccacc tcccg                                            25

<210> SEQ ID NO 7
<211> LENGTH: 26
<212> TYPE: DNA
<213> ORGANISM: artificial sequence
<220> FEATURE:
<223> OTHER INFORMATION: Primer CLPH5470

<400> SEQUENCE: 7
atgctttggg gatccttggc aagaga                                           26

<210> SEQ ID NO 8
<211> LENGTH: 25
<212> TYPE: DNA
<213> ORGANISM: artificial sequence
<220> FEATURE:
<223> OTHER INFORMATION: Primer LPH5461

<400> SEQUENCE: 8
acccttctct gccaaggatc cccaa                                            25

<210> SEQ ID NO 9
<211> LENGTH: 40
<212> TYPE: DNA
<213> ORGANISM: artificial sequence
<220> FEATURE:
<223> OTHER INFORMATION: Primer CLPH6270

<400> SEQUENCE: 9
aaaagaattc ggacagtctt ctgtttttat tttcggaaaa                            40
```

METHOD OF TREATING LACTOSE INTOLERANCE USING GENETICALLY ENGINEERED BACTERIA

BACKGROUND OF THE INVENTION

Lactose Intolerance

Dairy foods are an important source of protein, riboflavin and calcium for the United States, Europe, Asia, Africa and the many other areas of the world. However, many individuals suffer from lactose intolerance. This condition results from absence or insufficient production of the enzyme lactase. Acquired lactase deficiency is the most common disorder of complex carbohydrate absorption throughout the world, affecting up to 75% percent of the world's population. In the United States, 15% of Caucasians, over 50% of Hispanics and over 80% of African Americans suffer from lactose intolerance. The disorder is characterized by gastrointestinal symptoms of excessive gas production, abdominal pain, cramps, bloating and diarrhea after excessive consumption of lactose-containing foods such as dairy and dairy-based products.

In infancy, mammals have a high level of lactase activity in the lining of the upper intestinal tract, because they depend on lactose as the primary carbohydrate in their diet. However, in humans, the lactase expression is diminished by about 90% between ages two and five. This condition is called primary lactase deficiency. Many Northern Europeans, some Western Europeans, Mediterraneans and their descendants carry a mutation that prevents this natural decrease in lactase production. These individuals are able to consume milk as adults. However, large portions of the world population, such as Southern Europeans, East Asians and Sub-Saharan Africans have primary lactase deficiency.

Secondary lactase deficiency results from injury or disease of the small intestine. For example, celiac disease, inflammatory bowel syndrome (IBS) and Crohn's disease are often accompanied by lactase deficiency. These diseases occur in all ethnic groups.

Lactose Metabolism

Lactose is a disaccharide of glucose and galactose linked by a beta-D-glycosidic bond. The disaccharide is digested into its individual sugars by the lactase (beta-D-galactosidase) produced in the small intestine by the cells of the intestinal brush border. Glucose and galactose are absorbed in the small intestine. When lactase is absent from the small intestine, undigested lactose reaches the large intestine. There the resident bacteria metabolize lactose through fermentation generating gas. The gas is responsible for symptoms such as pain, pressure, cramps and flatulence. In addition, the undigested lactose increases osmotic pressure in the intestine, causing increased excretion of water and diarrhea.

Supplementing Lactase

There are several ways of delivering lactase to the gastrointestinal tract. As a simplest method, one can ingest a tablet of the isolated enzyme. Enzymes that break down lactose may be isolated from a variety of microorganisms, such as yeast, bacteria and fungi, such as *Saccharomyces fragilis, Torula cermoris, Lactobacillus bulgaricus, Aspergillus oryzae, Aspergillus flavus* and *Asperillus niger*. For example, U.S. Pat. No. 2,762,749 teaches preparing a lactase enzyme from budding yeast (*Saccharomyces* and *Torula* genuses) to supplement milk products where lactose crystallization is a problem. Lactase from fungi, such as *Aspergillus*, is described in U.S. Pat. No. 3,620,924. Isolating bacterial lactase (from the genus *Bacillus*) is described in U.S. Pat. Nos. 4,179,335, 4,237,230 and 4,323,651.

Several problems are associated with lactase replacement products. First, these products are not retained in the gastrointestinal tract. Lactase pills must be taken with each diary-containing meal. When the subject forgets to take the pill, or is unaware that food contains dairy, the symptoms of lactose intolerance are bound to recur.

Another problem is that many lactase enzymes from other species function poorly in the mammalian small intestine. The pH of the duodenum, where most of the normal lactose digestion occurs, is between 6.0 and 6.5. In contrast, as taught in the U.S. Pat. No. 6,562,339, a fungal lactase has a pH optimum of 4.8 and is only 10% active at pH 6.5. Many bacterial beta-galactosidases have a pH optimum above 7.0. Fortunately, a few enzymes from the *Bacillus* genus, as described for example, in U.S. Pat. No. 4,179,335, have a pH optimum near 6.0.

Another way to supplement lactase involves ingesting live or killed lactase-producing bacteria. For example, it is known that persons with mild lactose intolerance are able to tolerate yogurt but not milk, although both products contain the same amount of lactose. This is due to the fact that bacteria present in yogurt, such as *Streptococcus thermophilus, Lactobacilli, Acidophilus* and *Bifidus* species, express functional lactase. Thus, to improve the ability to digest lactose, one may consume yogurt products containing live and active cultures of these bacteria. Alternatively, one can ingest capsules that contain lyophilized live yogurt bacteria, as taught for example, in the U.S. Pat. No. 6,008,027. For an enhanced effect, bacteria can be combined with isolated lactase in the same enterically coated capsule, as taught in the U.S. Pat. No. 5,952,021 or Application Publication No. 2005/0100535.

Besides yogurt bacteria, other lactase-producing species can be used to improve lactose tolerance. For example, Korean researchers have isolated strains with lactase activity and good resistance to gastric acid. These strains come from *Lactobacillus fermentum*, (WIPO Publication KR3064030A), *Lactococcus lactis* (WIPO Publication KR4044300A) and *Lactobacillus plantarum* (WIPO Publication KR2088797A).

Unfortunately, physicians report limited success with treating lactose intolerance with naturally occurring bacterial cultures. The review of the literature conducted by family practitioners at the University of Pittsburg ("Do probiotics reduce adult lactose intolerance?" J Fam. Pract., 2005; v. 54, No. 7, p. 613-620) concluded that overall, the strategy was ineffective. The authors suggest that this is due to variation in bacterial viability and ability to produce lactase between the different dairy products and supplements. According to the study, with a few exceptions, most of these products do not provide sufficient lactase activity to alleviate the symptoms of lactose intolerance.

The symptoms of lactose intolerance were not relieved even when the most promising bacterium, *Lactobacillus acidophilus* was used. Among the yogurt bacteria, *L. acidophilus* has one of the highest natural levels of lactase and superior ability to adhere to the intestinal wall. Nevertheless, a Tufts University study "A randomized trial of *Lactobacillus acidophilus* BG2F04 to treat lactose intolerance", Am. J. Clin. Nutr. 1999, 69:140-146, concluded that even this bacterium was ineffective against the symptoms of lactose intolerance.

Using genetically-engineered bacteria to digest lactose is also known in the art. For example, U.S. Pat. No. 6,833,260 describes bacteria engineered to produce bacterial beta-galactosidase under the control of a constitutive promoter. Compared to the parent strain, the engineered bacteria produce more enzyme, although it is still of bacterial origin.

A more aggressive method of treating lactose intolerance involves gene therapy where the lactase gene is delivered directly into the cells of the intestinal wall, as described in U.S. Pat. No. 6,110,456. This method has several disadvantages. First, virus-driven gene therapy carries its own risks associated with the vector and the helper virus. Second, the target cells for the therapy, the intestinal epithelium, are constantly shedding. Unless the stem cells at the base of the inner layer of the intestinal wall are transformed with the new gene, the expression of lactase will be temporary. The newly emerging layers of intestinal cells would need to be repeatedly retransformed with another dose of the gene.

In summary, there is a need for a safe but long-lasting treatment of lactose intolerance. Ideally, one treatment would last for months without re-application. An ideal treatment would involve a lactase enzyme optimized for action under the conditions found in the mammalian small intestine.

SUMMARY OF THE INVENTION

The present invention relates to genetically engineered bacteria that are able to colonize the mammalian intestine and actively produce mammalian enzymes for the hydrolysis of lactose. The lactose-digesting enzymes are stable and active under the conditions normally found in the mammalian small intestine.

DEFINITIONS

"Small intestine" is the part of the gastrointestinal tract between the stomach and the large intestine. In vertebrate animals, small intestine is composed of duodenum, jejunum, and ileum.

"Large intestine" is the final part of the gastrointestinal tract in vertebrate animals.

"Resident bacteria" or "resident bacterial microflora" refers to bacteria that naturally colonize a host organ, such as gastrointestinal tract, or genetically altered strains of such bacteria.

"Gene" is the segment of DNA involved in producing a polypeptide chain; it includes regions preceding and following the coding sequence.

"Polypeptide" or "protein" is a polymer of amino acid residues encoded by at least a portion of the coding sequence of the gene.

"Enzymatically active protein" refers to a polypeptide that has enzymatic activity i.e. can catalyze specific chemical reactions of the proper substrates under proper conditions either within or outside of a cell where the polypeptide is produced.

"Genetically engineered bacteria" refers to bacterial cells that replicate a heterologous nucleic acid, or express a polypeptide encoded by a heterologous nucleic acid.

"Heterologous nucleic acid" is one that originates from a source foreign to the particular host cell, or, if from the same source, is modified from its original form.

"Promoter" is a nucleic acid sequence that acts as a signal sequence necessary to initiate transcription of a gene.

"Gene expression" as referred to in this application is the transcription (production of mRNA) followed by translation (production of a polypeptide encoded by the gene).

"Plasmid" is circular double-stranded DNA molecule, separate from chromosomal DNA and capable of autonomous replication and stable propagation in the host cell.

"Lactic acid bacteria" is a group of bacterial species comprised of Gram positive, low-GC-content, acid tolerant, non-sporulating, non-respiring rods or cocci that produce lactic acid as the major metabolic end-product of carbohydrate fermentation. This group includes the genera of *Lactobacillus, Leuconostoc, Pediococcus, Lactococcus, Streptococcus, Aerococcus, Carnobacterium, Enterococcus, Oenococcus, Teragenococcus, Vagococcus,* and *Weisella*.

"Homolactic lactic acid bacteria" are a subgroup of lactic acid bacteria that catabolize one mole of glucose through glycolysis (Embden-Meyerhof-Parnas (EMP) pathway) to yield two moles of pyruvate that is further reduced to lactate. This subgroup includes the genera of *Lactococcus, Enterococcus, Streptococcus* and *Pediococcus*.

DETAILED DESCRIPTION OF THE INVENTION

The present invention provides intestine-colonizing bacteria, such as for example, *Lactobacillus acidophilus,* that are genetically altered to express mammalian lactase activity. Using genetically-engineered lactic acid bacteria has several advantages over the prior art method of lactase supplementation. First, bacteria are able to self-replicate while retaining the inserted lactase gene. Second, lactic acid bacteria are normally present in milk and yogurt have been proven safe over the millennia since humans have been ingesting these foods.

Bacterial Strains

The preferred embodiment involves the use of bacterium *Lactobacillus acidophilus*, however other related or similar species found in dairy products may also be used. The suitable bacteria belong to the group homolactic Lactic Acid Bacteria (LAB). Representative homolactic LAB genera include *Lactococcus, Enterococcus, Streptococcus, Pediococcus* and group I *lactobacilli*. Common examples from this group include *Lactobacillus acidophilus, Lactobacillus delbrueckii* subsp. *bulgaricus* (often referred to as *L. bulgaricus*), *Bifidobacterium lactis* and *Streptococcus thermophilus*.

*Lactobacillus acidophilus* was originally isolated from feces of infants. It can also be isolated from mouth and vagina of children and adults. In other animals, this bacterium can be found in the intestinal tract of turkeys and chickens and mouth and intestinal tract of rats and hamsters. A strain of this species is available from American Tissue Culture Collection (ATCC) as #53544. The strain was transformed with a recombinant genetic construct incorporating a coding sequence for a mammalian lactase.

Lactase Gene

The mammalian gene selected for this invention is a human gene encoding lactase-phlorizin hydrolase (LPH) (Mantei, et al., *EMBO J.* 7:2705-2713 (1988)). LPH, sometimes called small-intestinal lactase, is a major digestive enzyme in the small intestine of newborns. The enzyme is first synthesized as a 215-245 kDa precursor, comprising four tandemly repeated domains (I-IV). Proteolytic cleavage of the precursor separates LPH-alpha (domains I-II), devoid of enzymatic function, and liberates the mature enzyme, LPH-beta consisting of domains III and IV. LPH-beta has enzymatic activity and is anchored to the membrane via a C-terminal hydrophobic segment.

The lactase activity can be measured in vitro by any number of well-known methods. One method utilizes O-nitrophenyl-beta-D-galactopyranoside (ONPG) as a substrate and spectrophotometrically measures the product O-nitrophenol (ONP). The amount of ONP is then divided by the reaction time and the weight of the reaction mixture or the number of cells in the reaction. A unit of lactase activity can be expressed in umol ONP/min per gram of dry weight.

Genetic Construct

The invention utilizes standard molecular biology techniques described in Sambrook et al., Molecular Cloning, A Laboratory Manual (3$^{rd}$. ed., 2001).

The genetic construct used for this invention is based on a plasmid vector pRLU61, capable of replicating in Gram-positive bacteria. See Jost et al., Biochem. J. 327:95-103 (1997).

The mRNA sequence of human LPH (in the cDNA form) has a Genebank accession no. X07994, and is reproduced below as SEQ. ID NO. 1.

Plasmid pS1234T (FIG. 1) was constructed by inserting the LPH cDNA (EcoRI fragment) into the unique EcoRI site of pRLU61. The full-length cDNA sequence of LPH was cloned as described in the Examples section. In the pS1234T, the LPH coding sequence is driven by a constitutive CMV promoter.

Figure 1:
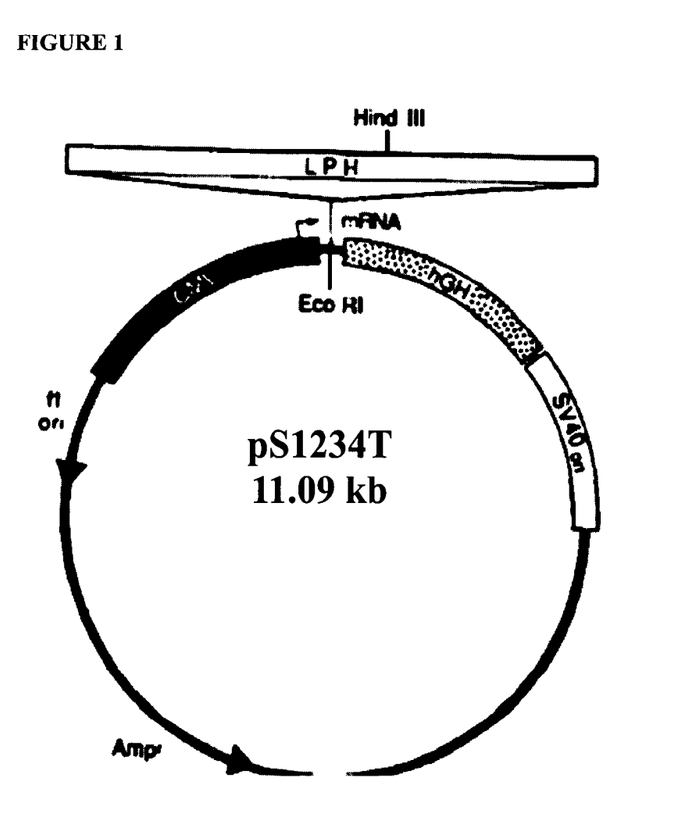
FIG. 1 is a map of the plasmid pS1234T.

The full-length precursor of LPH (domains I-IV) contained a proteolytic cleavage signal between domains II and III. When introduced into the host cells, the precursor was cleaved by the host proteases as evidenced by the appearance of measurable lactase activity. The plasmid produced expression of LPH in both prokaryotic and eukaryotic cells, including rat epithelial cells and Chinese hamster ovary (CHO) cells and bacterial cells as further described below.

Experimental Animals

Rats (Sprague Dawley) were used for this experiment. The animals were divided into six groups: Groups A and B received no treatments and served as controls. Groups C and D ingested genetically engineered *Lactobacillus acidophilus*. Groups E and F ingested wild-type *Lactobacillus acidophilus*. In Groups C and E, prior to ingestion of the bacteria, the animal's gut was flushed with antibiotics for a day. Then the bacteria were ingested on the following day. This treatment enables the bacteria to gain competitive advantage over the preexisting microflora and take up residence in the small intestine.

After bacteria were given time to colonize the intestine, the animals were fed lactose-containing foods and their blood glucose level was monitored. At the same time, blood lactase activity was measured spectrophotometrically using ONPG as a substrate. As shown in Table 1, animals colonized with genetically engineered *Lactobacillus acidophilus* (Groups C and D) demonstrated the highest levels of lactase activity as measured directly and evidenced by the appearance of blood glucose.

Table 1 shows weekly measurements of blood glucose and lactase activity following the initial ingestion of bacteria. After a 12-hour overnight fast, the animals were fed lactose-containing food. A duplicate measurement was taken at each of the indicated time points in minutes after the animals consumed lactose-containing food. The measurements were taken weekly for five weeks (W1-W5). Blood glucose is expressed in mg/dL, lactase activity is expressed in units equal to umol ONP/min per gram of dry weight

TABLE 1

Blood Glucose and Lactase Activity

| | Blood Glucose | | | | | Lactase Activity | | | | |
|---|---|---|---|---|---|---|---|---|---|---|
| Min | W1 | W2 | W3 | W4 | W5 | W1 | W2 | W3 | W4 | W5 |
| Group C (antibiotics pre-treatment and GE bacteria) | | | | | | | | | | |
| 0 | 125 | 125 | 125 | 125 | 125 | 110 | 110 | 110 | 110 | 110 |
|  | 125 | 125 | 125 | 125 | 125 | 110 | 110 | 110 | 110 | 110 |
| 30 | 160 | 161 | 160 | 160 | 160 | 116 | 120 | 120 | 120 | 120 |
|  | 160 | 160 | 161 | 161 | 175 | 116 | 121 | 120 | 120 | 120 |
| 60 | 175 | 177 | 170 | 175 | 180 | 135 | 135 | 136 | 136 | 136 |
|  | 175 | 177 | 170 | 176 | 181 | 135 | 136 | 136 | 136 | 136 |
| 90 | 180 | 185 | 180 | 180 | 190 | 130 | 130 | 130 | 130 | 130 |
|  | 180 | 185 | 182 | 180 | 190 | 130 | 130 | 130 | 130 | 130 |
| 120 | 190 | 190 | 190 | 190 | 190 | 140 | 142 | 140 | 140 | 140 |
|  | 190 | 190 | 191 | 190 | 190 | 140 | 142 | 140 | 140 | 140 |
| Group D (GE bacteria) | | | | | | | | | | |
| 0 | 125 | 125 | 125 | 125 | 125 | 110 | 110 | 110 | 110 | 110 |
|  | 125 | 125 | 125 | 125 | 125 | 110 | 110 | 110 | 110 | 110 |
| 30 | 160 | 160 | 160 | 160 | 160 | 130 | 130 | 130 | 130 | 128 |
|  | 160 | 160 | 160 | 160 | 160 | 130 | 130 | 130 | 130 | 128 |
| 60 | 185 | 185 | 180 | 180 | 180 | 160 | 160 | 160 | 160 | 160 |
|  | 185 | 185 | 180 | 180 | 180 | 160 | 160 | 160 | 160 | 160 |
| 90 | 185 | 180 | 180 | 180 | 180 | 180 | 180 | 180 | 180 | 180 |
|  | 185 | 180 | 180 | 180 | 180 | 180 | 180 | 180 | 180 | 180 |
| 120 | 180 | 180 | 185 | 185 | 180 | 180 | 180 | 180 | 180 | 180 |
|  | 180 | 180 | 185 | 185 | 180 | 180 | 180 | 180 | 180 | 180 |
| Group E (antibiotics pre-treatment and wild-type bacteria) | | | | | | | | | | |
| | Blood Glucose, mg/dL | | | | | Lactase Activity | | | | |
| Min | W1 | W2 | W3 | W4 | W5 | W1 | W2 | W3 | W4 | W5 |
| 0 | 125 | 125 | 125 | 125 | 125 | 110 | 110 | 110 | 110 | 110 |
|  | 125 | 125 | 125 | 125 | 125 | 110 | 110 | 110 | 110 | 110 |
| 30 | 140 | 140 | 135 | 130 | 130 | 120 | 125 | 125 | 120 | 120 |
|  | 140 | 140 | 135 | 130 | 130 | 120 | 125 | 125 | 121 | 120 |

TABLE 1-continued

Blood Glucose and Lactase Activity

| 60  | 160 | 160 | 161 | 160 | 160 | 130 | 130 | 130 | 135 | 130 |
|-----|-----|-----|-----|-----|-----|-----|-----|-----|-----|-----|
|     | 160 | 160 | 160 | 160 | 160 | 130 | 130 | 130 | 135 | 130 |
| 90  | 170 | 170 | 171 | 170 | 170 | 140 | 145 | 145 | 140 | 140 |
|     | 170 | 170 | 170 | 170 | 170 | 140 | 145 | 145 | 141 | 140 |
| 120 | 175 | 175 | 172 | 170 | 170 | 140 | 145 | 140 | 140 | 145 |
|     | 175 | 174 | 173 | 175 | 170 | 140 | 145 | 145 | 140 | 141 |

Group F (wild-type bacteria)

| Minutes | Blood Glucose, mg/dL | | | | | Lactase Activity | | | | |
|---|---|---|---|---|---|---|---|---|---|---|
| | W1 | W2 | W3 | W4 | W5 | W1 | W2 | W3 | W4 | W5 |
| 0 | 125 | 125 | 125 | 125 | 125 | 110 | 110 | 110 | 110 | 110 |
|   | 125 | 125 | 125 | 125 | 125 | 110 | 110 | 110 | 110 | 110 |
| 30 | 135 | 135 | 135 | 135 | 135 | 125 | 120 | 125 | 125 | 125 |
|    | 135 | 135 | 135 | 135 | 135 | 125 | 120 | 125 | 125 | 125 |
| 60 | 160 | 170 | 160 | 160 | 160 | 135 | 130 | 130 | 128 | 130 |
|    | 160 | 170 | 160 | 160 | 160 | 135 | 130 | 130 | 128 | 130 |
| 90 | 170 | 150 | 160 | 160 | 160 | 140 | 135 | 138 | 135 | 135 |
|    | 170 | 150 | 160 | 160 | 160 | 140 | 135 | 138 | 135 | 135 |
| 120 | 175 | 175 | 165 | 165 | 165 | 140 | 145 | 135 | 135 | 135 |
|     | 175 | 175 | 165 | 165 | 165 | 140 | 145 | 135 | 135 | 135 |

Next, lactase activity in the stool was measured. As shown in Table 2, animals colonized with genetically engineered *Lactobacillus acidophilus* (Groups C and D) demonstrated the highest levels of lactase activity in the stool.

Table 2 shows weekly measurements of stool lactase activity following the initial ingestion of bacteria. A duplicate measurement was taken each week. The measurements were taken weekly for seven weeks (W1-W7). Lactase activity is expressed in units equal to umol ONP/min per gram of dry weight. The gender of the animals is also indicated as M or F.

TABLE 2

Stool Lactase Activity

| | W1 | W2 | W3 | W4 | W5 | W6 | W7 |
|---|---|---|---|---|---|---|---|
| Group A (Control) | | | | | | | |
| M | 110 | 110 | 110 | 110 | 110 | 110 | 110 |
| M | 110 | 110 | 110 | 110 | 110 | 109 | 109 |
| F | 110 | 110 | 110 | 110 | 110 | 109 | 109 |
| F | 110 | 110 | 110 | 110 | 110 | 110 | 109 |
| Group B (Control) | | | | | | | |
| M | 110 | 110 | 110 | 109 | 110 | 110 | 110 |
| M | 110 | 110 | 110 | 109 | 110 | 110 | 110 |
| F | 109 | 110 | 110 | 110 | 110 | 110 | 110 |
| F | 109 | 110 | 110 | 110 | 110 | 110 | 110 |
| Group C (antibiotics pre-treatment and GE bacteria) | | | | | | | |
| M | 202 | 200 | 202 | 202 | 202 | 202 | 202 |
| M | 202 | 200 | 202 | 202 | 202 | 202 | 202 |
| F | 202 | 201 | 201 | 202 | 202 | 202 | 202 |
| F | 202 | 201 | 201 | 202 | 202 | 202 | 202 |
| Group D (GE bacteria) | | | | | | | |
| M | 175 | 175 | 172 | 172 | 169 | 169 | 165 |
| M | 175 | 175 | 172 | 172 | 169 | 169 | 165 |
| F | 175 | 175 | 172 | 172 | 169 | 169 | 164 |
| F | 175 | 175 | 172 | 172 | 169 | 169 | 164 |
| Group E (antibiotic pre-treatment and wild-type bacteria) | | | | | | | |
| M | 150 | 150 | 149 | 150 | 136 | 136 | 136 |
| M | 150 | 150 | 149 | 149 | 136 | 136 | 136 |
| F | 150 | 149 | 150 | 150 | 136 | 136 | 136 |
| F | 150 | 149 | 150 | 150 | 136 | 136 | 136 |
| Group F (wild-type bacteria) | | | | | | | |
| M | 160 | 160 | 160 | 160 | 135 | 138 | 135 |
| M | 160 | 160 | 160 | 160 | 135 | 138 | 135 |
| F | 160 | 160 | 160 | 160 | 138 | 137 | 135 |
| F | 160 | 160 | 160 | 160 | 138 | 138 | 135 |

Finally, the animals were sacrificed and the intestinal lactase activity was measured directly. As shown in Table 3, animals colonized with genetically engineered *Lactobacillus acidophilus* (Groups C and D) demonstrated the highest levels of lactase activity in the extracts.

Table 3 shows lactase activity in umol ONP/min per gram of dry weight. For each animal a sample was taken from the stomach as well as two sections of the small intestine: duodenum and jejunum. The time is measured after the consumption of lactose-containing foods, following a 12-hour overnight fast. Experimental Groups A-F are as described above. The gender of animals is indicated as M or F.

TABLE 3

Lactase Activity in Intestinal Sections

| Study Group | Intestinal sections | Lactase activity | | | |
|---|---|---|---|---|---|
| | | 0 min | 60 min | 90 min | 120 min |
| Group A | Stomach | 0.09 | 0.08 | 0.06 | 0.03 |
|  | Duodenum | 0.07 | 0.81 | 0.60 | 0.10 |
|  | Jejunum | 0.04 | 0.13 | 0.14 | 0.16 |
| Group B | Stomach | 0.08 | 0.09 | 0.05 | 0.04 |
|  | Duodenum | 0.08 | 0.91 | 0.81 | 0.10 |
|  | Jejunum | 0.04 | 0.14 | 0.15 | 0.16 |
| Group C | Stomach | 0.65 | 0.60 | 0.75 | 0.65 |
|  | Duodenum | 0.44 | 0.89 | 0.95 | 1.04 |
|  | Jejunum | 0.33 | 1.44 | 1.52 | 1.67 |
| Group D | Stomach | 0.65 | 0.63 | 0.60 | 0.65 |
|  | Duodenum | 0.44 | 0.90 | 0.99 | 1.05 |
|  | Jejunum | 0.35 | 1.45 | 1.55 | 1.70 |

TABLE 3-continued

Lactase Activity in Intestinal Sections

| Study Group | Intestinal sections | Lactase activity | | | |
|---|---|---|---|---|---|
| | | 0 min | 60 min | 90 min | 120 min |
| Group E | Stomach | 0.42 | 0.45 | 0.50 | 0.40 |
| | Duodenum | 0.35 | 0.70 | 0.80 | 0.95 |
| | Jejunum | 0.20 | 0.99 | 1.02 | 1.30 |
| Group F | Stomach | 0.36 | 0.39 | 0.40 | 0.40 |
| | Duodenum | 0.29 | 0.69 | 0.71 | 0.92 |
| | Jejunum | 0.20 | 0.98 | 1.01 | 1.20 |

In addition, the microflora from different parts of the intestine was plated on the nutrient medium to assess the numbers of genetically engineered bacteria. As shown in Table 4, animals colonized with genetically engineered *Lactobacillus acidophilus* (Groups C and D) had the highest numbers of lactase-positive bacteria in the duodenum. There were no lactase-positive bacteria in the duodenum of the untreated animals (Groups A and B). Animals treated with wild-type *Lactobacillus acidophilus* (Groups E and F) had fewer lactase-positive bacteria in the duodenum than Groups C and D. In addition, Group C had the highest number of lactase-positive bacteria in the jejunum.

Table 4 shows the number of colony-forming units (CFUs) recovered from the intestinal extracts of each animal. The male and female animals in each group were used for each data point. Experimental Groups A-F are as described above. Each CFU is equal to 10 milion bacterial cells ($1 \times 10^7$ cells).

TABLE 4

Bacteria Recovered from Intestinal Sections

| Study Group | Intestinal sections | Bacterial counts CFU/ml |
|---|---|---|
| Group A | Stomach | 0 |
| | Duodenum | 0 |
| | Jejunum | 10 |
| Group B | Stomach | 0 |
| | Duodenum | 0 |
| | Jejunum | 25 |
| Group C | Stomach | 0 |
| | Duodenum | 10 |
| | Jejunum | 30 |
| Group D | Stomach | 0 |
| | Duodenum | 15 |
| | Jejunum | 25 |
| Group E | Stomach | 0 |
| | Duodenum | 5 |
| | Jejunum | 10 |
| Group F | Stomach | 0 |
| | Duodenum | 6 |
| | Jejunum | 15 |

Although the background information describes lactose intolerance in relation to humans, the invention is not meant to be so limited. Other mammals, such as dogs, cats and rodents suffer from the same type of primary lactose intolerance in adulthood. Thus one of ordinary skill in the art would be able to use the teachings of this invention to develop a similar treatment of lactose intolerance in such mammals.

The present invention teaches genetically engineered bacteria that must be ingested in order to aid in the digestion of lactose. For oral administration, the composition containing the bacteria of the present invention may be enclosed in an enterically coated capsule.

Such capsules are well known in the art. For example, U.S. Pat. No. 5,633,012 describes methods of microencapsulating lyophilized *lactobacilli* using alginate, polyacryl and a variety of other organic polymers. U.S. Pat. No. 5,952,021 teaches encapsulating bacteria in a methylacrylate-based polymers sold under the brand names EUDRAGIT S® and EUDRAGIT L®. These polymers are insoluble in acid, but dissolve at neutral pH found in the small intestine.

As is demonstrated above, to maximize the competitive advantage of the ingested bacteria, a subject may be pre-treated with an antibiotic before the bacterial culture is administered. Suitable antibiotics are, for example amoxicillin and neomycin As an alternative to lyophilization, the genetically engineered bacteria may be ingested as a live culture. The bacteria may be suspended in nutrient medium or prepared as a dairy product. Such products containing live bacteria are well known in the art. For example, Bio-K+ International, Inc. of Laval, Quebec, sells ½ oz cups of a yogurt-like product that contains a concentrated culture (up to 50 billion) of live and active cultures of *lactobacilli*. The cultures of the bacteria of the present invention may be prepared as a similar dairy product.

To maximize the survival of live cultures during the passage through the stomach, a subject may be pre-treated with a simple antacid such as baking soda or Alka-Seltzer® or an acid-reducing medication, such as omperazole sold by Merck & Co. under the brand name PRILOSEC®.

EXAMPLES

The following examples are meant to illustrate but not limit the invention.

Bacterial Strains

Bacterial strain was isolated from raw milk. The cultures were grown at 37° C. The optimum temperature is 35-38° C. The upper limit of temperature tolerance is about 48° C., the lower limit is above 22° C., as no significant growth is observed at 22° C. Growth occurs at initial pH values between 5.0 and 7.0, but the optimum pH range is 5.5-6.0.

The cultures were grown in Terrific Broth medium (per liter: 12 g bacto-tyrptone, 24 g yeast extract, 4 ml glycerol, 0.017M $KH_2PO_4$, 0.072M $K_2HPO_4$). Biochemical characteristics of this species are as follows: it metabolizes arginine into ammonia; ferments lactose into galactose and glucose, which in turn is further fermented into lactic acid; and also ferments amygdalin, cellobiose, fructose, galactose and maltose.

Genetic Construct

Figure 2:
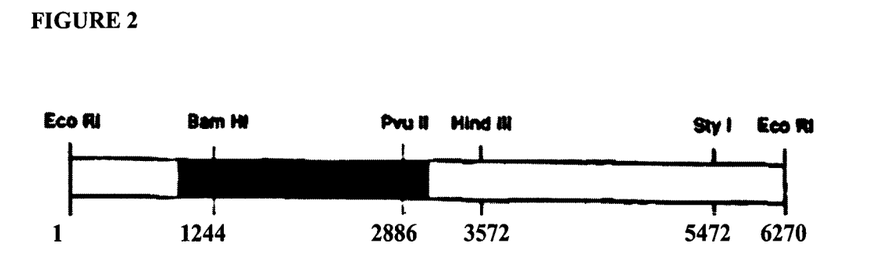
FIG. 2 is a detailed map of the insert in the plasmid pS1234T.

The plasmid pS1234T for expression in *L. acidophilus* was obtained by first assembling an insert (FIG. 2) in an *E. coli* plasmid PLPH. The plasmid PLPH was prepared in six steps.

First, screening of an intestinal cDNA library resulted in isolation of a 2,400 bp clone that contained a BamHI/PvuII fragment encompassing the putative LPH cleavage site. The BamHI/PvuII fragment was isolated for cloning.

Second, an EcoRI/BamHI fragment, corresponding to the nucleotides 1-1244 of the LPH cDNA was amplified by PCR using oligonucleotides LPH1 (SEQ ID NO. 2) and cLPH1300 (SEQ. ID NO. 3). This fragment was cloned into a commercially available vector pGEM4Z, generating a plasmid pLPH1. pLPH1 contained nucleotides 1-1244 of LPH cDNA.

Third, a PvuII/HindIII fragment corresponding to the nucleotides 2886-3572 of the LPH cDNA was amplified by PCR using oligonucleotides LPH2841 (SEQ ID NO. 4) and cLPH3600 (SEQ ID NO. 5). This PvuII/HindIII fragment and the isolated BamHI/PvuII fragment described in the first paragraph of this section were cloned by three-way ligation into pLPH1, using the BamHI and HindIII sites, generating a plasmid pLPH2. pLPH2 contained nucleotides 1-3572 of LPH cDNA.

Fourth, a HindIII/StyI fragment corresponding to the nucleotides 3572-5472 of the LPH cDNA was amplified by PCR using oligonucleotides LPH3541 (SEQ ID NO. 6) and cLPH5470 (SEQ. ID NO. 7).

Fifth, an StyI/EcoRI fragment corresponding to the nucleotides 5472-6270 of the LPH cDNA was amplified by PCR using oligonucleotides LPH5461 (SEQ ID NO. 8) and cLPH6270 (SEQ. ID NO. 9). This StyI/EcoRI fragment and the HindIII/StyI fragment described in the preceding paragraph were cloned by three-way ligation into pGEM4Z, using the EcoRI and HindIII sites, generating a plasmid pLPH3. pLPH3 contained nucleotides 3572-6270 of LPH cDNA.

Finally, the EcoRI/HindIII fragment from pLPH2 (nucleotides 1-3572 of LPH cDNA) and the HindIII/EcoRI fragment from pLPH3 (nucleotides 3572-6270 of LPH cDNA) were ligated in a three-way ligation into the EcoRI site of pGEM4Z, generating pLPH. The plasmid pLPH contained a full cDNA sequence of LPH.

```
LPH1 (SEQ ID NO. 2)
5'-AAAGAATTCGTTCCTAGAAAATGGAGCTGTCTTGGCATGTAG-3';

cLPH1300 (SEQ ID NO. 3)
5'-CTGGCCACCTCCAGCGTCGCTTGGC-3'

LPH2841 (SEQ ID NO. 4)
5'-AAAGACAATGCCACTGGAGACATCG-3' cLPH3600 (SEQ ID NO. 5)
5'-TGAACCTCTTCTCTTCCTCAGTGAA-3'

LPH3541 (SEQ ID NO. 6)
5'-AACTGCAGCACTTAGCCACCTCCCG-3' cLPH5470 (SEQ ID NO. 7)
5'-ATGCTTTGGGGATCCTTGGCAAGAGA-3'

LPH5461 (SEQ ID NO. 8)
5'-ACCCTTCTCTGCCAAGGATCCCCAA-3' cLPH6270 (SEQ ID NO. 9)
5'- AAAAGAATTCGGACAGTCTTCTGTTTTTATTTTCGGAAAA-3'
```

For experimental expression in mammalian cells, the full-length PH sequence (EcoRI fragment containing nucleotides 1-6270) was subcloned into the EcoRI site of pCMV2 (Invitrogen, Carlsbad, Calif.) to generate pS1234T (FIG. 1).

Experimental Animals

Sprague Dowley rats were housed under standard conditions and fed a standard diet. Water was given ad libitum. For Groups D and F, the animals were pre-treated with amoxicillin or neomycin. For all groups, except control groups A and B, a suspension of bacterial cells was given with yogurt as food.

At the end of 14 weeks the animals were sacrificed. The following parameters were measured during the course of the study: blood glucose concentration, lactase activity in the blood and stool, blood pH and total body weight. At the end of the study, lactase activity in the intestinal contents and the composition of intestinal microflora were also measured.

Measuring Blood Glucose Concentration

To measure blood glucose concentration, blood was taken from the tail vein. 0.7 ml was collected from each animal. The test was done using a blood glucose meter.

Measuring Blood, Stool and Intestinal Lactase Activity

The lactase activity was determined by United States Pharmacopeia (USP) method (USP27, official monograph pages 1062-1063). The stool was dispersed in buffer prior to the assay. Sections of the intestine were dissected and the contents were dispersed in buffer prior to the assay.

Counting the Number of Lactococci in the Intestine

The numbers of genetically engineered *lactococci* and wild-type *lactococci* were measured by suspending the intestinal contents and plating serial dilution of the suspensions on solid medium. The *lactococci* were detected by microscopic examination of the bacterial flora under Olympus inverted microscope based on the bacterial cell's morphology. The genetically engineered *lactococci* were detected.

The above examples are provided to illustrate the invention and not to limit its scope. Other variants of the invention will be readily apparent to one of ordinary skill in the art and are encompassed by the appended claims.

What is claimed is:

1. A composition for treating lactose intolerance in a mammal, comprising *Lactobacillus acidophilus* bacteria that are genetically modified to express a mammalian lactase-phlorizin hydrolase enzyme under the control of a CMV promoter, wherein said genetically modified *Lactobacillus acidophilus* bacteria have an enhanced ability to adhere to the intestinal surface than *Lactobacillus acidophilus* bacteria that are not genetically modified.

2. The composition of claim 1, wherein said intestinal surface is within the small intestine.

3. The composition of claim 1, wherein said *Lactobacillus acidophilus* bacteria are present as a live suspension.

4. The composition of claim 1, wherein said *Lactobacillus acidophilus* bacteria are present as a lyophilized powder.

5. The composition claim 4, further comprising an acid resistant coating.

* * * * *